US00PP21929P2

(12) United States Plant Patent
Lindsey

(10) Patent No.: US PP21,929 P2
(45) Date of Patent: May 24, 2011

(54) ***ABELIA* PLANT NAMED 'RADIANCE'**

(50) Latin Name: *Abelia×grandiflora*
Varietal Denomination: RADIANCE

(76) Inventor: Randall Dale Lindsey, Locust, NC (US)

( * ) Notice: Subject to any disclaimer, the term of this patent is extended or adjusted under 35 U.S.C. 154(b) by 0 days.

(21) Appl. No.: 12/660,863

(22) Filed: Mar. 4, 2010

Related U.S. Application Data

(60) Provisional application No. 61/209,869, filed on Mar. 12, 2009.

(51) Int. Cl.
*A01H 5/00* (2006.01)

(52) U.S. Cl. ..... Plt./226

(58) Field of Classification Search ..... Plt./226
See application file for complete search history.

*Primary Examiner* — Annette H Para

(57) ABSTRACT

A new cultivar of *Abelia* plant named 'RADIANCE' that is characterized by dense compact habit and bi-colored variegated foliage. In combination these traits set 'RADIANCE' apart from all other existing varieties of *Abelia* known to the inventor.

3 Drawing Sheets

Genus: *ABELIA*.
Species: ×*grandiflora*.
Denomination: 'RADIANCE'.

BACKGROUND OF THE INVENTION

This application claims the benefit of priority under 35 U.S.C. 119(e) of U.S. Provisional Application No. 61/209,869 filed on Mar. 12, 2009, entitled *Abelia* Plant Named 'RADIANCE'. The present invention relates to a new and distinct cultivar of *Abelia* grown as an ornamental plant for use in the landscape. The new cultivar is known botanically as *Abelia×grandiflora* and will be referred to hereinafter by the cultivar name 'RADIANCE'.

'RADIANCE' was discovered in 2006 as a naturally occurring branch sport which the inventor observed growing on an individual plant of *Abelia×grandiflora* 'Kaleidoscope' (U.S. Plant Pat. No. 16,988). The parent plant was located within a large commercial crop of 'Kaleidoscope' which was in production at the inventor's employer's nursery in Marshville, N.C.

'RADIANCE' can be readily distinguished from 'Kaleidoscope' by foliage color in particular. Whereas a single leaf of 'Kaleidoscope' exhibits multiple colors, a single leaf of 'RADIANCE' exhibits just two colors. In addition, 'RADIANCE' does not develop the fiery red foliage colors which are characteristic of the fall color of 'Kaleidoscope'.

Other than the parent plant, 'Kaleidoscope', the three closest comparison plants to 'RADIANCE' known to the Inventor are the variegated *Abelia* cultivars *Abelia×grandiflora* 'Sunrise' (U.S. Plant Pat. No. 9,698) and *Abelia×grandiflora* 'Conti' (U.S. Plant Pat. No. 8,472) and *Abelia×grandiflora×chinensis* 'Mardi Gras' (U.S. Plant Pat. No. 15,203).

In comparison with 'Sunrise', 'RADIANCE' exhibits similar stem color but is markedly lower growing. Whereas 'RADIANCE' a height of 70 cm in three years, 'Sunrise' grows to a height of 120 cm-125 cm in the same period. Additionally, the variegated band on the leaf of 'RADIANCE' is cream in color (except for the earliest new growth of unexpanded leaves) whereas the foliage of 'Sunrise' bears a yellow variegation throughout its growing cycle.

In comparison with 'Conti', 'RADIANCE' exhibits similar plant habit and eventual height and spread. However, the stems of 'RADIANCE' are red in color whereas the stems of 'Conti' are purplish in color. Additionally, the flowers of 'RADIANCE' are approximately twice as large (in length and width) than the flowers of 'Conti'.

'Mardi Gras', which is an inter-specific hybrid, exhibits pink coloration to the whole plant especially in spring. The young foliage of 'Mardi Gras' bears pink variegation and the calyces and buds of 'Mardi Gras' are also pink in color. 'RADIANCE' does not exhibit any pink coloration to its foliage or flowers.

'RADIANCE' was first asexually propagated in 2006 by the inventor in North Carolina. Asexual propagation was accomplished using softwood cuttings. Since that time, under careful observation, the distinguishing characteristics of 'RADIANCE' have been determined stable and uniform, and are reproduced true to type in successive generations of asexual reproduction.

SUMMARY OF THE INVENTION

The distinguishing characteristics of 'RADIANCE' are as follows: In combination these traits set 'RADIANCE' apart from all other existing varieties of *ABELIA* known to the inventor. 'RADIANCE' has not been tested under all possible conditions and phenotypic differences may be observed with variations in environmental, climatic, and cultural conditions.

1. 'RADIANCE' exhibits variegated foliage with individual leaves which are bi-colored.
2. The new foliage growth of 'RADIANCE' is predominantly mid green with gold-yellow margins.
3. The mature foliage of 'RADIANCE' is predominantly gray-green with cream margins.
4. 'RADIANCE' exhibits vivid crimson stems in its current year's growth and red-brown stems thereafter.
5. 'RADIANCE' is approximately 70 cm. in height and 120 cm. in width at maturity.
6. 'RADIANCE' fragrant white flowers that bloom from mid summer into fall.
7. 'RADIANCE' exhibits dense compact habit.
8. 'RADIANCE' is suitable for use as a low accent plant, mass plantings in the landscape, and as a container plant.
9. 'RADIANCE' is hardy to at least in USDA Zone 7.

BRIEF DESCRIPTION OF THE DRAWINGS

The accompanying color drawings illustrate the overall appearance of 'RADIANCE' showing the colors of its foliage and flowers as true as it is reasonably possible to obtain in colored reproductions of this type.

The drawing labeled

Figure 1:
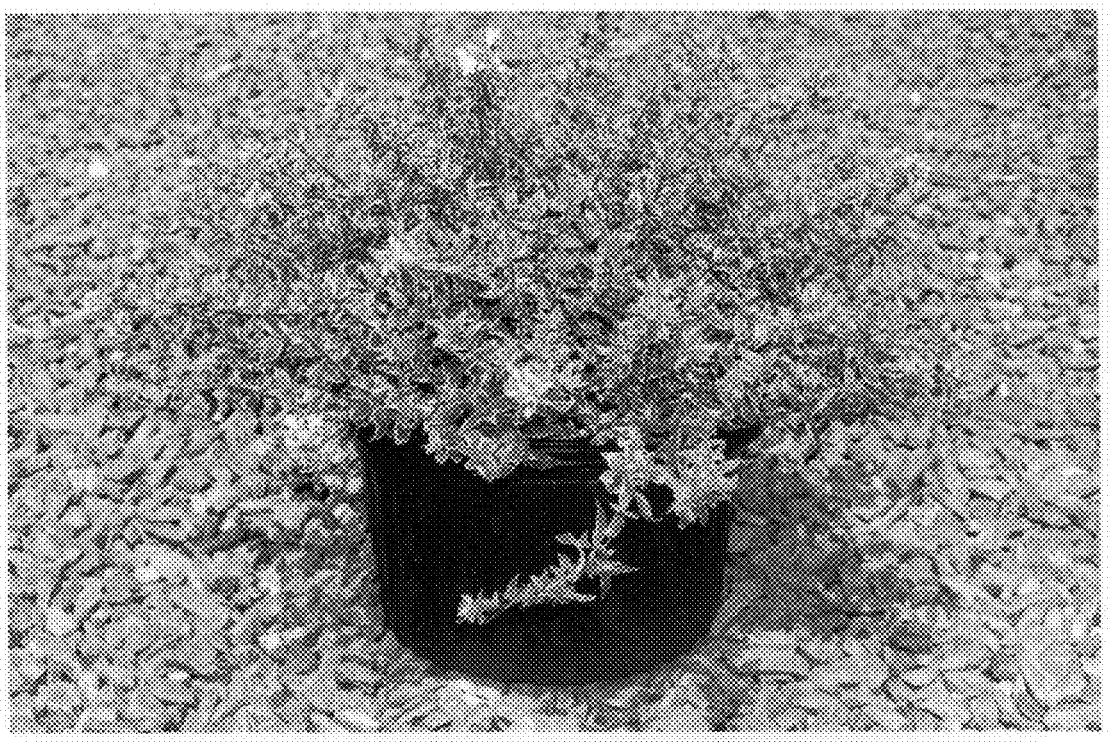
FIG. 1 shows a two-year old plant of 'RADIANCE' which has been grown out of doors in a 3 gallon container in Marshville, N.C. and exhibiting the typical dense, compact mounding habit of 'RADIANCE'.
Figure 2:
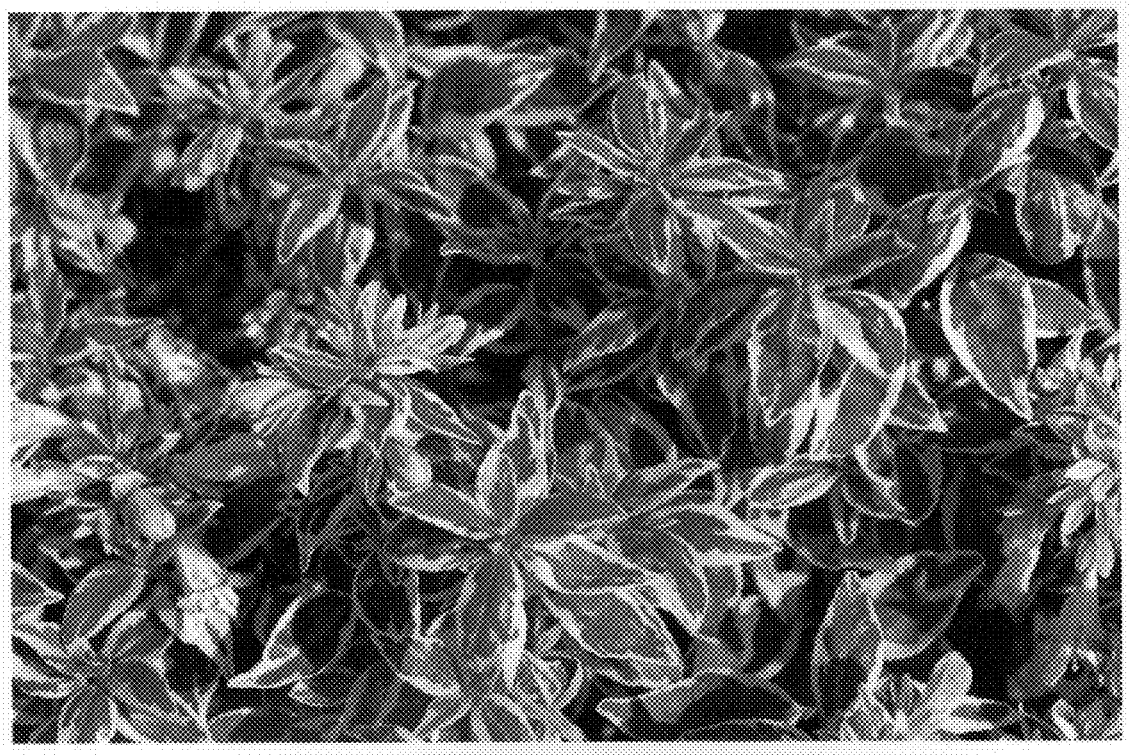

The drawing labeled as FIG. 2 depicts a close-up view of the foliage of 'RADIANCE'.

Figure 3:
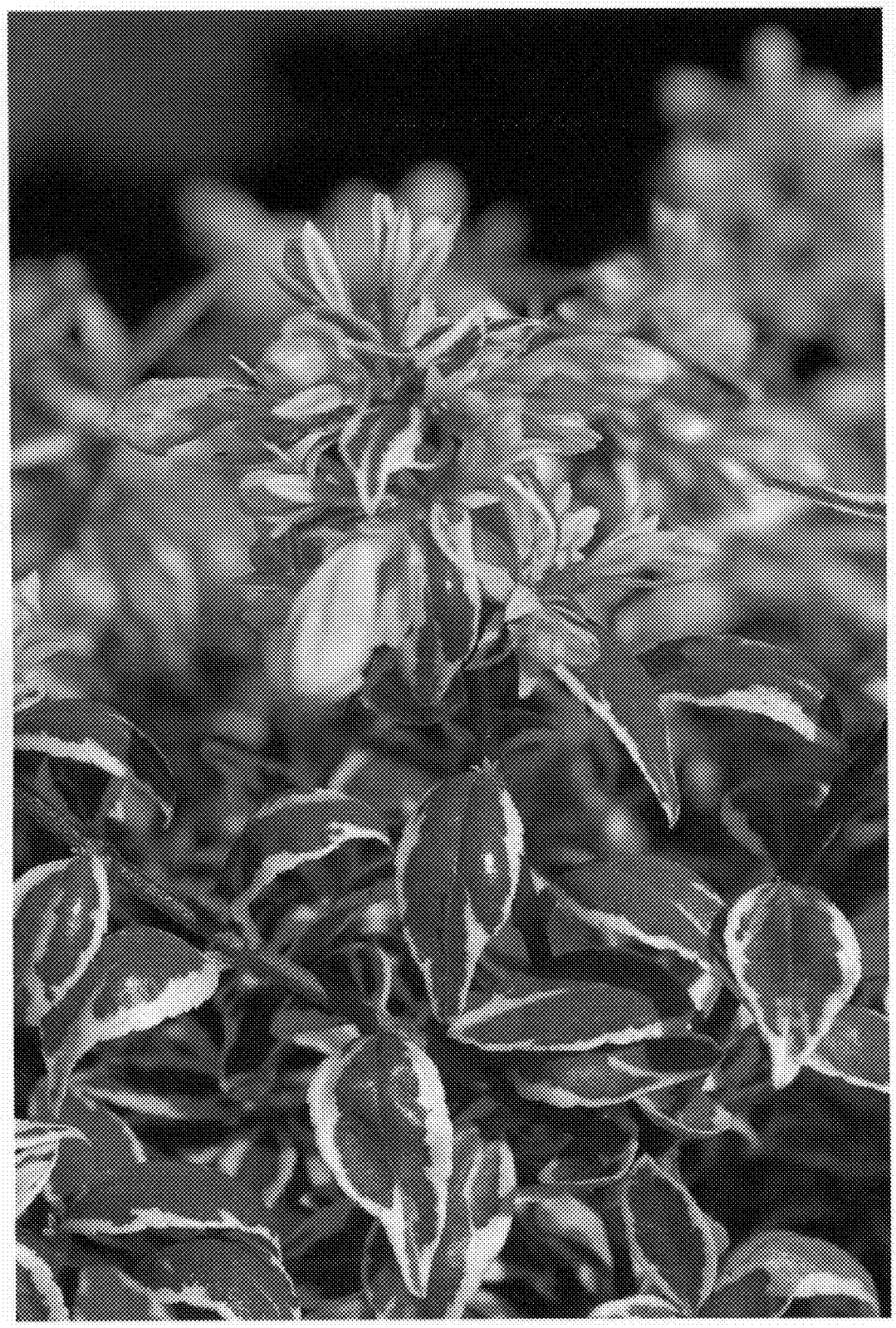

The drawing labeled as FIG. 3 depicts a close up view of the current year's growth and shows the vivid crimson color of the stems. This drawing also depicts the early stages of development of the terminal inflorescence of 'RADIANCE'.

All the drawings have been made from photographs taken by conventional techniques and although foliage colors may appear different from actual colors due to light reflectance, they are as accurate as possible by conventional photography.

BOTANICAL DESCRIPTION OF THE PLANT

The following is a detailed description of the *Abelia×grandiflora* cultivar named 'RADIANCE' using observations of two and three year old plants of 'RADIANCE' which have been grown in 3 gallon containers and also in the landscape in full sun in Marshville, N.C. Color determinations are in accordance with The 2002 Edition of he Colour Chart of The Royal Horticultural Society, London, England, except where general color terms of ordinary dictionary significance are used. 'RADIANCE' has not been tested under all possible conditions and phenotypic differences may be observed with variations in environmental, climatic, and cultural conditions, however, without any variance in genotype. The growing requirements are similar to the species.

Botanical classification: *Abelia×grandiflora* 'RADIANCE'.

Genus: *Abelia.*

Species: *×grandiflora.*

Denomination: 'RADIANCE'.

Commercial classification: Ornamental shrub.

Common name: Glossy *abelia.*

Uses: Low accent plant and mass plantings in the landscape, and as a container plant.

Container size: Suggested container size is 3 gallons in order to produce a well-formed two year old plant.

Cultural requirements: Plant in acidic and well-drained moist soil. Full sun enhances vibrancy of foliage color, but plants will grow in partial shade.

Parent: 'RADIANCE' was discovered as a naturally occurring branch sport on an individual plant of *Abelia×grandiflora* 'Kaleidoscope' (U.S. Plant Pat. No. 16,988).

Plant description:

*Blooming season.*—From mid summer into fall.

*Plant habit.*—Dense and compact.

*Vigor.*—Vigorous.

*Plant form.*—Mounding.

*Plant height* (*at maturity*).—Averages 70 cm when established in the landscape for three years.

*Plant width* (*at maturity*).—Averages 120 cm when established in the landscape for three or four years.

*Hardiness.*—Hardy at least to USDA Zone 7; not tested in colder regions.

*Propagation.*—Softwood cuttings.

*Root system.*—Fibrous.

*Time to initiate roots.*—2 weeks are needed to produce roots on an initial cutting.

*Air temperature to develop roots on initial cuttings.*—An air temperature of 29° Centigrade is ideal to produce roots on initial cuttings.

*Crop time.*—4 months are needed to produce a liner plant in a 5cm-10cm plug or pot from an initial cutting. A liner plant can be potted and grown as a finished 1.5-2 liter container in a further 10-15 months.

*Seasonal interest.*—Fragrant white flowers from mid summer to fall, and a mix of vibrant leaf color from spring to fall and winter.

*Diseases and pests.*—May exhibit occasional moderate infection of *Botrytis* under conditions of high humidity and poor air circulation, as, for example, when plants are grown too closely together. Otherwise there are no serious diseases or pests known to the inventor.

*Growing requirements.*—Maintain good fertility to increase foliage retention in winter.

*Growing problems.*—None known to the inventor. Plant is easy to grow and requires little or no pruning to maintain dense compact mounding form.

Stem:

*Internode length.*—1.75 cm. between nodes.

*Stem diameter.*—At base of three year old plant: 25 mm. Current year growth: 3 mm-5 mm.

*Stem length.*—22 cm. in length.

*Shape.*—Cylindrical.

*Surface.*—Pubescent.

*Stem color.*—46A.

Foliage:

*Type.*—Evergreen to semi-deciduous.

*Leaf arrangement.*—Opposite and whorled.

*Leaf division.*—Simple.

*Leaf shape.*—Lanceolate.

*Leaf base.*—Rounded.

*Leaf apex.*—Acute.

*Leaf venation.*—Pinnate.

*Vein color* (*adaxial and abaxial surfaces*).—191C.

*Leaf surface* (*adaxial*).—Glabrous.

*Leaf surface* (*abaxial*).—Glabrous.

*Leaf appearance* (*abaxial surfaces*).—Semi-glossy.

*Leaf appearance* (*adaxial surfaces*).—Glossy.

*Leaf attachment.*—Petiolate.

*Petiole dimensions.*—3 mm. in length and 1 mm. in diameter.

*Petiole color.*—Colors 162A and 35A are both present on an individual plant.

*Petiole shape.*—Sulcate.

*Petiole surface.*—Glabrous.

*Leaf margin.*—Crenate.

*Leaf length.*—Leaves on an individual plant range from 1.5 cm. in length to 3.25 cm. in length.

*Leaf width.*—Leaves on an individual plant range from 6 mm. in width to 1.50 cm. in width.

*Leaf colors* (*new growth, leaves not fully expanded, both surfaces*).—Centers of individual leaves: 143A with yellow-gold variegated marginal band, 14A which extends from 1 mm-2 mm from margin.

*Leaf colors* (*all other stages, both surfaces*).—Centers of individual leaves: 138B or 191A with cream variegated marginal band, 158D which extends from 2 mm-3 mm from margin.

*Foliar fragrance.*—None observed.

Flower:

*Inflorescence.*—Terminal panicles.

*Flower depth.*—2.50 cm. in depth.

*Flower diameter.*—2.25 cm in diameter.
*Corolla tube dimensions.*—2 cm. in length and 0.75 cm. in diameter.
*Corolla tube surface* (*inner surface*).—Pubescent.
*Corolla tube surface* (*outer surface*).—Glabrous.
*Corolla tube color* (*inner and outer surfaces*).—N155B.
*Petals.*—Five in number.
*Petal surface* (*adaxial surface*).—Pubescent.
*Petal surface* (*abaxial surface*).—Glabrous.
*Petal color* (*abaxial and adaxial surfaces*).—N155B.
*Petal apex.*—Rounded.
*Petal margins.*—Entire.
*Petal dimensions.*—0.75 cm. in length and 0.50 cm. in width.
*Petals fused or unfused.*—Basally fused.
*Flower shape.*—Funnelform.
*Flower color.*—N155B.
*Quantity of flowers.*—A range of 1-6 flowers per panicle.
*Persistent or self-cleaning.*—Self-cleaning.
*Color of peduncle.*—165C.
*Peduncle length.*—3 cm. in length.
*Peduncle diameter.*—2mm. in diameter.
*Surface of peduncle.*—Puberulent.
*Pedicel color.*—182A.
*Pedicel dimensions.*—5 mm. in length and 0.75 mm. in width.
*Aspect.*—Facing outward and downward.
*Bud shape.*—Club-shaped.
*Bud color* (*immature*).—154A with stripes of 144B.
*Bud color* (*mature, as flower opens*).—1D becoming 155A with flecking 47B which disappears when flower fully open.
*Bud surface.*—Puberulent.
*Bud dimensions.*—11 mm. in length and 4 mm. in diameter.
*Calyx shape.*—Stellate.
*Color of calyx.*—145A.
*Surface of calyx.*—Puberulent.
*Sepals.*—Five in number.
*Sepal dimensions.*—9 mm. in length and 3 mm. in width.
*Sepal margins.*—Entire.
*Sepal shape.*—Oblanceolate.
*Sepal apex.*—Acute.
*Sepal base.*—Cuneate.
*Sepal color.*—145A.
*Sepals fused or unfused.*—Unfused.
*Blooming period.*—Mid summer into fall.
*Fragrance.*—Perfume fragrance.

Reproductive organs:
*Stamens.*—Four stamens in number.
*Stamen shape.*—Filament.
*Dimensions of stamen.*—2.25 cm. in length and less than 0.50 mm. in width.
*Color of stamen.*—N155B.
*Dimensions of anther.*—1 mm. in width and 0.50 mm. in length.
*Pollen color.*—N155B.
*Amount of pollen.*—Small amount.
*Anther color.*—156A.
*Anther shape.*—Turbinate.
*Pistil.*—One.
*Color of pistil.*—N155B.
*Pistil shape.*—Filament.
*Dimensions of pistil.*—2.25 cm. in length and less than 0.50 mm. in diameter.
*Ovary position.*—Inferior.
*Ovary color.*—143A.
*Ovary shape.*—Oblong.
*Ovary dimensions.*—2 mm. in diameter and 6 mm. in length.
*Ovary surface.*—Puberulent.

Seed: No seed has been observed to date.

The invention claimed is:

1. A new and distinct variety of *Abelia* plant named 'RADIANCE' as described and illustrated.

* * * * *